United States Patent [19]
Zanger

[11] Patent Number: 5,971,918
[45] Date of Patent: Oct. 26, 1999

[54] DEVICE FOR THE PHOTODYNAMIC ENDOSCOPIC DIAGNOSIS OF TUMOR TISSUE

[75] Inventor: Ulf Zanger, Weingarten, Germany

[73] Assignee: Richard Wolf GmbH, Knittlingen, Germany

[21] Appl. No.: 08/911,075

[22] Filed: Aug. 14, 1997

[30] Foreign Application Priority Data

Oct. 2, 1996 [DE] Germany ............... 196 40 700

[51] Int. Cl.⁶ ............................................. A61B 1/06
[52] U.S. Cl. ..................... 600/160; 600/181; 600/476
[58] Field of Search ..................... 600/109, 160, 600/181, 182, 407, 476, 478, 178

[56] References Cited

U.S. PATENT DOCUMENTS

| | | |
|---|---|---|
| 4,807,026 | 2/1989 | Nishioka et al. |
| 5,255,087 | 10/1993 | Nakamura et al. ............... 600/109 |
| 5,684,908 | 11/1997 | Kross et al. ............... 385/125 |

FOREIGN PATENT DOCUMENTS

| | | |
|---|---|---|
| 0 478 026 A1 | 4/1992 | European Pat. Off. . |
| 29 17 436 A1 | 11/1980 | Germany . |
| 41 33 493 A1 | 4/1992 | Germany . |
| 42 28 106 A1 | 3/1994 | Germany . |
| 195 12 518 A1 | 10/1995 | Germany . |
| 196 08 027 A1 | 9/1996 | Germany . |
| 195 39 829 A1 | 4/1997 | Germany . |
| 1-136629 | 5/1989 | Japan . |
| 1-136630 | 5/1989 | Japan . |
| 9-131305 | 5/1997 | Japan . |
| 2 288 123 | 10/1995 | United Kingdom . |

*Primary Examiner*—John P. Leubecker
*Attorney, Agent, or Firm*—Akin, Gump, Strauss, Hauer & Feld, L.L.P.

[57] ABSTRACT

The invention relates to a device for the photodynamic endoscopic diagnosis of human or animal tumor tissue with the help of a marker substance capable of fluorescence and with an endoscope and a light source. With this, means are provided in order to guide light from the light source via an endoscope to the diagnosis location in each case in one of at least two selectable spectral regions, that is in a white light region and in a region with blue-violet light, in order thus in each case to be able to carry out a visual examination with white light and stimulate a marker substance deposited in any tumor tissue to fluoresce. The means for selecting the light comprises an anti-fading filter which can be pivoted into the beam path of the white stimulation light on examination with white light and which filters out light, lying in spectral region stimulating fluorescence, from the white light. This anti-fading filter, together with other color filters may be mounted on a pivoting wing which can be selectively pivoted by the examining surgeon into the light path between the light source and the light guide cable, the pivoting wing being movable by way of a pivoting device.

8 Claims, 3 Drawing Sheets

DEVICE FOR THE PHOTODYNAMIC ENDOSCOPIC DIAGNOSIS OF TUMOR TISSUE

BACKGROUND OF THE INVENTION

The invention is concerned with the photodynamic diagnosis of tumor tissue and relates in particular to a device for the photodynamic endoscopic diagnosis of tumor tissue in the human or animal body with the help of a marker substance capable of fluorescence and with an endoscope as well as a light source. With this there are provided means in order to guide light from the light source via the endoscope to the diagnosis location in each case in one of at least two selectable spectral regions, that is the white light region and a region with blue-violet light, and in each case to be able to carry out a visual examination with white light and to stimulate a marker substance accumulated in any tumor tissue, to fluoresce.

With such a known device for tumor examination, a patient receives a systematic, oral, topical, instilled or otherwise enriched dosage of the dye δ-amino levulinic acid (ALA). After a given reaction time the body converts this substance into the dye porphyrine IX (PP IX). This preferably deposits itself in the regions changed by disease (DE 42 28 106 A). On illumination of the surface of the organ with light of a suitable spectral combination, the regions having a high PP IX concentration fluoresce with a red color and thus permit an easy detection and spacial definition of the diseased region.

The light which is suitable for stimulating PP IX contains only spectral components of approximately 380 to 445 nm, appears intensive blue-violet to the eye and thus is not very suitable for a normal diagnosis or for spacial orientation, e.g. in the body cavity to be examined, since it is desirable, before the diagnosis supported by fluorescence, to carry out a diagnosis under white light and to repeat this where appropriate. This means that the examining surgeon must be able to choose between these two operating types.

However by way of the intensive illumination of the surface of the organ the dye is broken down relatively quickly in the accumulation regions, by which means the fluorescence intensity is reduced and eventually completely disappears. This process is called "fading". Fading however occurs not only with illumination with blue light, i.e. in the blue light mode, but also with illumination with white light, in the white light mode, since the white light likewise contains fluorescence stimulating spectral components. With examination with white light the time thus available for an effective fluorescence diagnosis is reduced. Since the examination with white light is generally carried out first of all, it may even occur that the dye, i.e. the marker substance, has already faded before the first actuation of the actual stimulation light, due to which the flourescence supported diagnosis is no longer possible.

Moreover in some cases with the fluorescence examination in the blue light mode, the tumor does not distinguish itself clearly enough or unambiguously from healthy tissue. In such cases an increase in the contrast would be desirable.

From DE 196 08 027 A1 there is known a device for the photodynamic endoscopic diagnosis of tumor tissue. The examination is carried out with the known device in two operating modes, that is in the white light mode and in the blue light mode, however this is without a marker substance being led to the patient. In the light source there is located a stimulation light filter which only lets through light in a narrow wavelength band of 420 to 480 nm in order to be able to carry out a fluorescence observation on cancerous tissue with an endoscope. With observation in the white light region, this stimulation light filter is removed from the light path. To the endoscope there can be connected a televison camera unit which comprises a normal camera for taking a normal observation picture, i.e. in the white light region, and a fluorescence camera for taking a fluorescence picture. An optical system in the television camera unit contains a filter, for the fluorescence observation, which is arranged in front of the imaging lens, blocks off light with wavelengths which are let through by the stimulation light filter, and which only lets through light with wavelengths greater than 480 nm and smaller than 520 nm. Therefore only this light can reach the image intensifier of the fluorescence camera.

For producing fluorescent light, when biological tissue is illuminated with light in the region of 470 to 480 nm, this known device works in the region of the dimensional order of 480 to 600 nm with an intensity peak of 480 to 520 nm, wherein however cancerous tissue or other diseased tissue does not fluoresce. If the stimulation light filter is located in the beam path then only the fluorescing light produced by normal tissue of the object reaches the image intensifier of the fluorescence camera and is correspondingly intensified. Thus, because the device known from DE 196 08 027 A1 does not use a marker substance for marking the tumor tissue, the problem of fading of the marker substance does not occur.

DE 195 12 518 A1 describes an apparatus for treating tumors comprising a light source which emits a bundle of rays with ultraviolet, visible and infrared radiation. An infrared filter as well as a filter for visible radiation are arranged in front of a light guide which directs the filtered bundle of rays onto an affected tissue part. For treatment, the patient is enriched with Ti02 (titanium dioxide) which accumulates much more in tumor cells. Thus when the tumor cells are irradiated with electromagnetic waves of a wavelength from the X-ray region to ultraviolet, with this the Ti02 is stimulated so that the tumor cells are destroyed by the released active oxygen. Apart from the fact that the apparatus known from DE 195 12 518 A1 is used for the treatment and not the diagnosis of tumors, in none of the operating modes is a protective filter employed. The region which stimulates the Ti02 in the tumor cells (approx. 280 to 400 nm) is always completely let through.

BRIEF SUMMARY OF THE INVENTION

It is the object of this invention to so form a device of the type specified, for the photodynamic endoscopic diagnosis of tumor tissue with the help of a marker substance capable of fluorescence, that before and in breaks between photodynamic diagnosis, a normal visual diagnosis can be carried out without reducing the concentration of marker substance capable of fluorescence which is necessary for the fluorescence diagnosis.

This object is achieved in that with the visual diagnosis with white light, an anti-fading filter filtering light lying in the spectral region which stimulates fluorescence, can be pivoted in the beam path of the white light.

Preferably, the anti-fading filter only lets through light above a wavelength of the maximum absorption of the marker substance which has deposited itself. Usefully the edge of the anti-fading filter lies approximately between 420 to 460 nm. e.g. at about 430 nm.

In order to protect the eyes of the examining surgeon from the intensive blue light irradiated in the blue light mode, and so that the surgeon can observe the interesting, possibly red-flourescing tissue regions in the blue light mode, the endoscope contains a color filter which lets through spectral components which lie above a value lying in a region of 430 to 460 nm, and filters out the smaller wavelengths.

This color filter is preferably employed in the endoscope wherein this may concern a video endoscope or an optical endoscope. Basically, a conventional insert funnel endoscope may be used and the color filter can be accomodated in the ocular component which is to be inserted on. However, also endoscopes or video endoscopes with a rigid ocular funnel may be employed. Then the color filter may be arranged either distally or in the rigid ocular funnel. In order to minimize the transmission losses for the stimulating light, low-loss light guides are used in the light path of the stimulation light, as e.g. quartz light guides or fluid light guides.

Furthermore the invention provides for the light source to be switched over into a third operating mode, i.e. that selectively three filters are available. This third operating mode is selected in such cases in which the contrast of the tumor to the surrounding tissue is weak or when with the first two operating modes, despite suspicion of a tumor, none as such can be discovered. With this third operating mode, a contrast filter is pivoted into the light path of the blue-violet stimulation light, this contrast filter being so designed that it offers as high as possible color contrast of the tumor fluorescing in the red region to the neighbouring tissue. In this manner, there arises a darker background in front of which the fluorescing image components stand out particularly clearly. With this, one must still take care that as much blue-violet light as possible is let through in order to maintain the fluorescence appearance, since after the stimulation light is removed the substances used subsequently illuminate for a few nanoseconds at the most.

By way of the contrast filter, the long wave edge of the blue stimulation light in the spectral diagram may be shifted to the left, preferably up to below the short wave edge (435 nm) of the endoscope color filter.

In order to keep the intensity losses of the stimulation light as small as possible, alternatively a contrast filter may be employed which sets the long wave edge of the blue light to about 440 nm.

BRIEF DESCRIPTION OF THE DRAWINGS

Further features and advantages of the invention result from the subsequent description of an embodiment example illustrated in the drawings. There are shown.

DETAILED DESCRIPTION OF THE INVENTION

Figure 3:
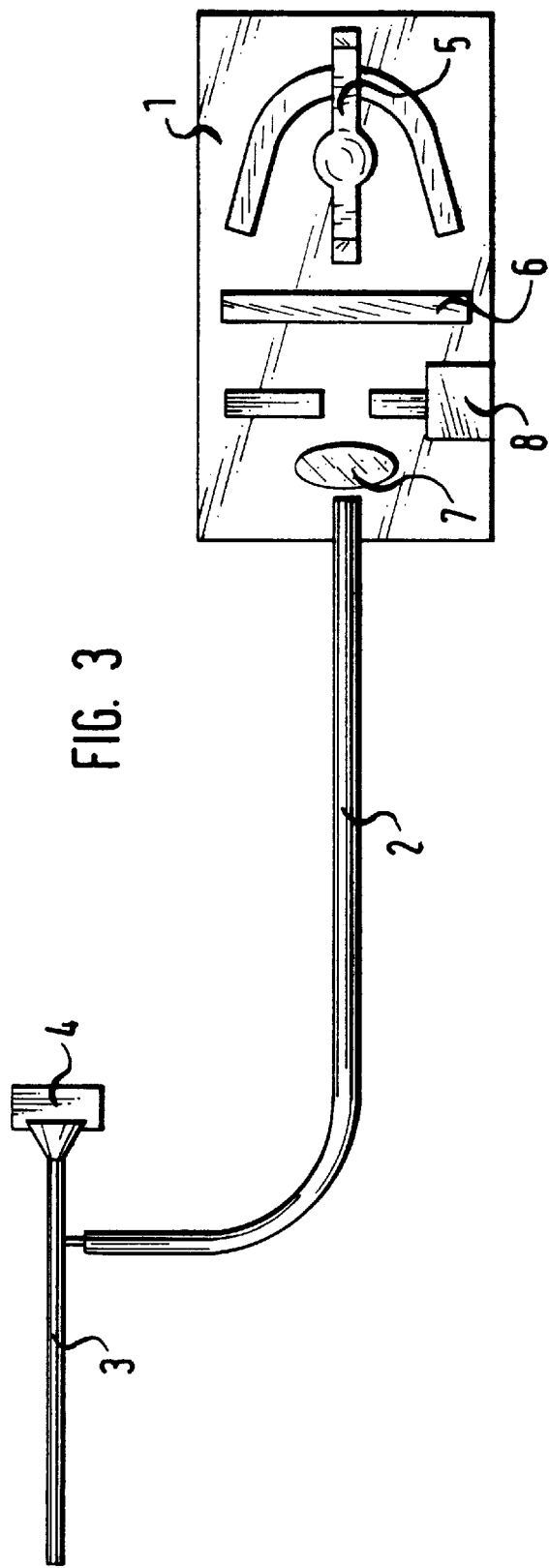

The device for the photodynamic analysis of tumor tissue comprises according to FIG. 3 essentially of a light source 1, a light guide cable 2 for connecting the light source 1 and an endoscope 3. The endoscope 3 on the ocular side is provided with a color filter 4 which only lets through blue-violet light in small quantities.

As a light guide, a quartz light guide or a fluid light guide are considered. Furthermore the light guide should ensure a particularly high transmission in the blue-violet spectral region.

Apart from electrical circuits (not shown), the light source 1 contains a lamp 5. An infrared filter 6 is arranged in the beam path in order to filter out damaging heat rays. Via a lens 7, the light is coupled into the proximal end of the light guide cable 2. This lens may be omitted when a self focusing lamp (DE 196 08 027 A) is employed. On the distal side of the infrared filter 6 there is provided a pivoting filter device 8 with which the filters corresponding to the choice of operating modes can be additionally pivoted into the beam path.

Figure 4:
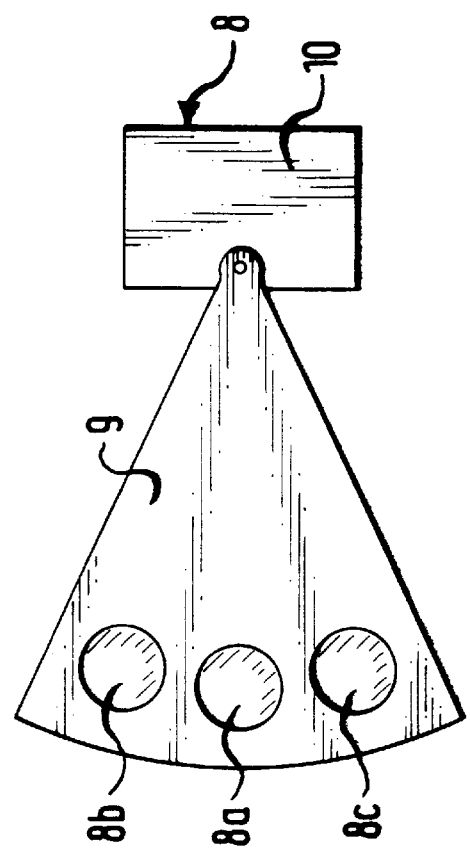

From FIG. 4 it can be recognized that the pivoting filter device 8 comprises three filters 8a, 8b and 8c which are arranged on a wing 9 which is movable by way of a pivoting device 10 known per se, so that selectively one of the filters 8a, 8b, 8c may be pivoted into the beam path from the lamp 5 to the light guide cable 2.

The wing 9 carries at least a filter 8b which is an anti-fading filter, and prefereably carries a filter 8a for the blue stimulation light (only blue light is let through), the filter 8b which as an anti-fading filter prevents the fading of the fluorescing substance, and a filter 8c which serves as a contrast filter for increasing the contrast between the red fluorescing and the other tissue regions.

Figure 1:
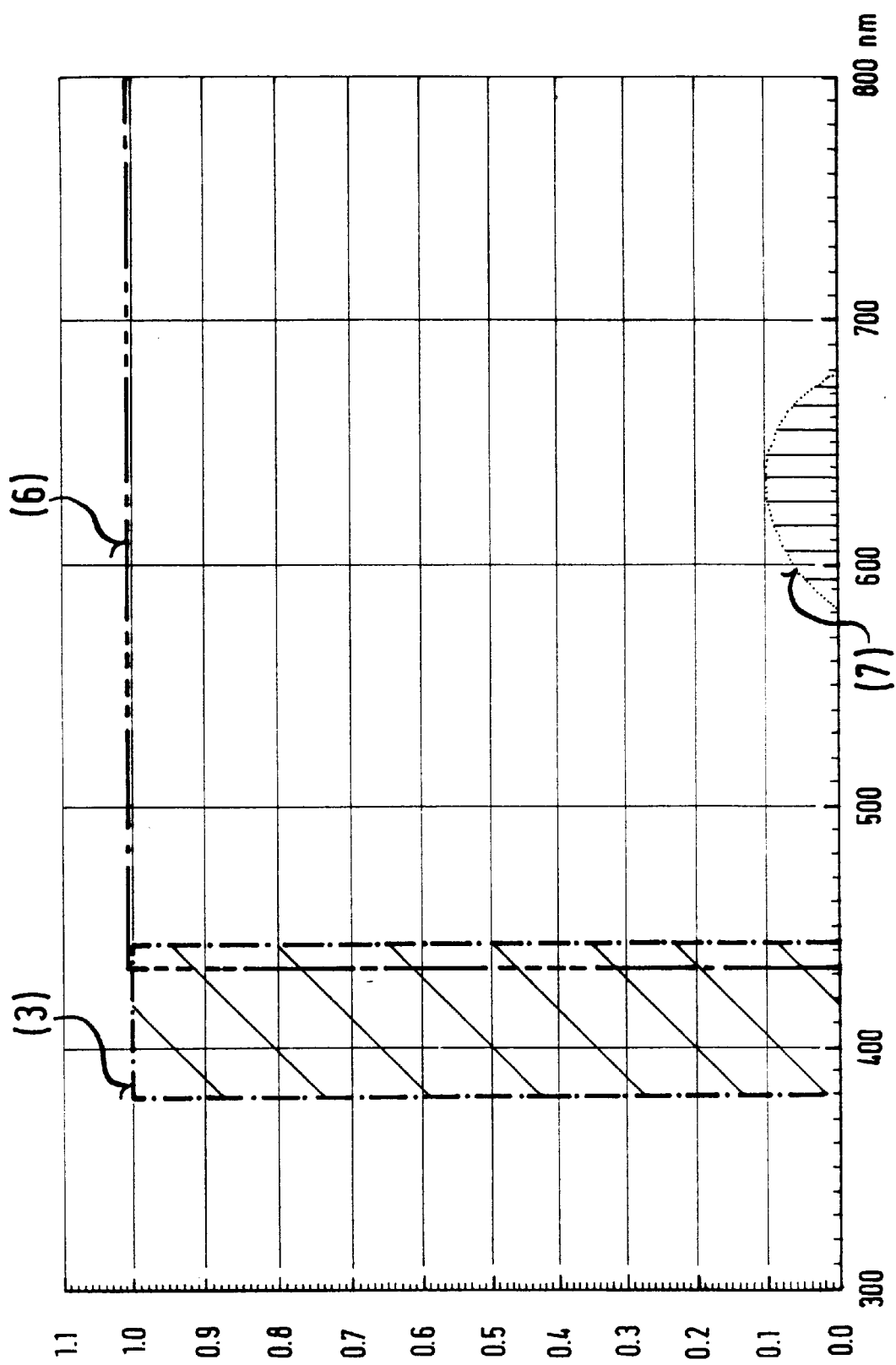
FIG. 1 a spectrum which schematically makes clear the spectral relationships in the blue light stimulation mode, FIG. 2 an expanded region of the spectrum between 340 and 500 nm, into which there is entered the absorption spectrum of PP IX in the tissue, normalized to the maximum absorption at about 407 nm, and additionally the integral of the absorption spectrum of PP IX, FIG. 3 schematically, the construction of the device according to the invention and FIG. 4 a filter device which is designed as a pivoting filter and permits a choice of the operating modes by pivoting several different light filters into the light path.

FIG. 1 shows the normalized spectral regions
of the blue stimulation light (3) of about 380 to 445 nm (diagonally hatched region),
the region (6), which the endoscope color filter (4) lets through, and
the region (7) of the red-violet fluorescent light (vertically hatched region). From this it is also clear that the relative intensity of the fluorescent light emitted from the marker dye in the tumor tissue is relatively slight.

Figure 2:
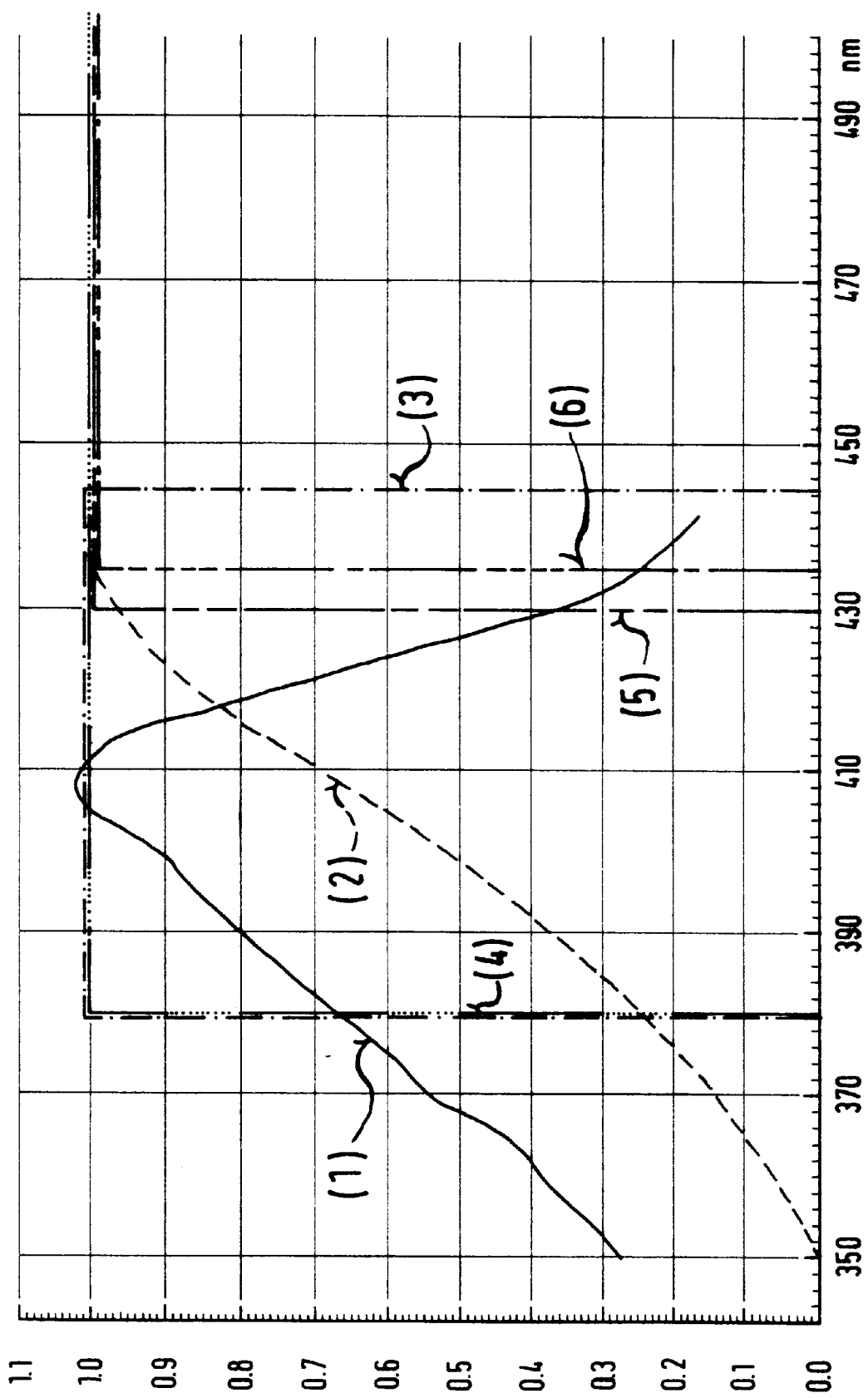

In FIG. 2 the region of the spectrum between 340 and 500 nm is reproduced in an expanded manner. Moreover the absorption spectrum of PP IX in the tissue is entered as a solid curve (1) and the integral of the absorption spectrum according to curve (1) is entered in the form of a dashed curve (2). Since the absorption spectrum is a measure of the fluorescence caused by a given stimulation wave-length, the curve (2) gives a value for the fluorescence intensity on stimulation with a wide spectrum. Thus the light source is so designed that in the blue light stimulation mode it covers the curve (1) as well as possible. Ultraviolet spectral components, i.e. such with a wavelength of below 380 nm, represent a potential danger and are thus not desired. Components above 440 nm hardly deliver any contribution to fluorescence stimulation, but may however reduce the color contrast. The stimulation light spectrum (3) thus advantageously goes from approximately 380 to 445 nm (dot-dashed framed region in FIG.2).

In the white light mode, the radiated spectrum (see region (4) in FIG. 2) of the light source 1 likewise begins at 380 nm and extends in the usual manner up to 700 nm. Longer-waved components (heat radiation) are filtered out. It is clear that this spectrum (4) of the white light mode stimulates the dye (marker substance) in the same way as the blue stimulation light and thus fades out the dye.

For this reason, according to the invention, in the white light mode the antifading filter 8b is pivoted into the beam path from the lamp 5 of the light source 1 to the light guide cable 2. In FIG. 2, the spectral region of the anti-fading filter 8b is entered as the region (5) and lies above about 435 nm. In this way the anti-fading filter in the white stimulation light only lets through light above a wavelength which lies above the maximum absorption of the PP IX serving as the marker substance (see curve (1)). By way of this there is only a slight stimulation of the marker substance and its fading is considerably delayed.

If the spectral edge, that is the short-waved edge of the anti-fading filter 8b, lies below, or at the most as high as that of the endoscope color filter 4 according to the spectral region (6) in FIG. 2, there does not result any additional color distortion of the white light image. Since the short-waved edge of the endoscope color filter 4 lies at about 430 to 460 nm, the edge of the anti-fading filter 8b may lie between 420 and 460 nm, and this according to FIG. 2 lying e.g. at 430 nm.

The contrast filter 8c mounted on the same pivoting wing 9, in a third operating mode, may be pivoted into the light path between the lamp 5 and the light guide cable 2. The contrast filter 8c serves for giving the observer as high as posssible contrast between the blue appearing healthy tissue and the red fluorescing diseased tissue. This contrast is at its best when the blue light is subdued as strongly as possible so that there arises a dark background against which the red fluorescing picture components distinguish themselves particularly clearly. However, as much blue light as possible must still be let through for stimulation in order to maintain the fluorescence appearance, since the substances accumulated in the tumor tissue which serve as markers hardly fluoresce at all after the stimulation light has ceased. For this purpose, the contrast filter 8c shifts the long-waved edge of the stimulation light towards the left, this being as much as possible up to 435 nm, i.e. below the short-waved edge of the endoscope color filter 4.

With an alternative contrast filter, the long-waved edge lies at about 440 nm in order to keep the intensity losses of the blue stimulation light as low as possible (cf. the course of the integral (2) with regard the absorption spectrum (1) in the region of 435 to 450 nm in FIG. 2). Although the blue stimulation light above the left short-waved edge of the endoscope color filter is completely or to a large extent supressed, enough blue stimulation light however may be irradiated onto the tissue to be examined, wherein no blue light or only blue light of a low intensity reaches the eye of the observer or the image receiving component of the video camera. Instead of this only the red fluorescing diseased tissue against a black background may be perceived. This operating mode is then particularly advantageous when the contrast between the tumor and the surrounding tissue is very weak or when in spite of the suspicion of a tumor, no tumor as such can be discovered with the first two operating modes.

I claim:

1. A device for photodynamic endoscopic diagnosis of tumor tissue through the use of a fluorescing marker substance, comprising an endoscope and a light source, the endoscope including a light guide adapted to guide light in one of at least two selectable spectral regions from a beam path of the light source to a diagnosis location, the at least two spectral regions include a white light region and a region with blue-violet light, such that the white light enables visual examination and the blue-violet light stimulates the fluorescing marker substance deposited in any tumor tissue to fluoresce, means for selecting one of the at least two selectable spectral regions, the means for selecting including an anti-fading filter pivotably mounted for movement into the beam path which filters light lying in the blue-violet region which would stimulate the fluorescing marker substance, wherein in the endoscope there is provided a color filter which lets through the reddish spectral region of a fluorescent light and filters out the blue-violet spectral components, and wherein a contrast filter suppresses light above a short-waved edge (about 430 nm) of the endoscope color filter and lets through blue-violet light below this wavelength.

2. A device according to claim 1, wherein the selecting means comprises a pivoting wing equipped at least with the anti-fading filter.

3. A device according to claim 2, wherein on the pivoting wing there is further provided a filter for blue-violet stimulation light.

4. A device according to claim 2, wherein the a contrast filter is on the pivoting wing, the contrast filter allowing a red spectral region of a stimulating light to pass through and filters out spectral components in the blue-violet region.

5. A device according to claim 1, wherein the color filter only lets through spectral components which lie above a value lying in the region of 430 to 460 nm.

6. A device according to 1, wherein the short-waved edge of the passband of the anti-fading filter lies between about 420 to 460 nm.

7. A device according to claim 1, wherein the light guide is a quartz light guide.

8. A device according to claim 1, wherein the light guide is a fluid light guide.

* * * * *